United States Patent
Martin et al.

(10) Patent No.: US 11,499,914 B2
(45) Date of Patent: Nov. 15, 2022

(54) MULTI-CHANNEL GAS SENSOR

(71) Applicant: Senseair AB, Delsbo (SE)

(72) Inventors: Hans Martin, Delsbo (SE); Henrik Rödjegård, Johanneshov (SE)

(73) Assignee: Senseair AB, Delsbo (SE)

( * ) Notice: Subject to any disclaimer, the term of this patent is extended or adjusted under 35 U.S.C. 154(b) by 0 days.

(21) Appl. No.: 17/619,730

(22) PCT Filed: Jun. 9, 2020

(86) PCT No.: PCT/SE2020/050589
§ 371 (c)(1),
(2) Date: Dec. 16, 2021

(87) PCT Pub. No.: WO2020/263155
PCT Pub. Date: Dec. 30, 2020

(65) Prior Publication Data
US 2022/0205906 A1 Jun. 30, 2022

(30) Foreign Application Priority Data
Jun. 25, 2019 (SE) .................................. 1950779-7

(51) Int. Cl.
*G01N 21/3518* (2014.01)
*G01N 21/3504* (2014.01)
*G01N 33/497* (2006.01)

(52) U.S. Cl.
CPC ..... *G01N 21/3518* (2013.01); *G01N 21/3504* (2013.01); *G01N 33/4972* (2013.01)

(58) Field of Classification Search
CPC .................. G01N 21/3518; G01N 21/3504
(Continued)

(56) References Cited

U.S. PATENT DOCUMENTS 3,594,583 A * 7/1971 Sheldon ................. G01H 9/002
250/363.01
3,869,613 A * 3/1975 Link ................... G01N 21/3518
250/343
(Continued)

FOREIGN PATENT DOCUMENTS

CN 1384350 A 12/2002
DE 4302385 C2 * 10/2003 ........... G01N 21/274
(Continued)

OTHER PUBLICATIONS

Q.-L. Tan et al., "Design of Mini-Multi-Gas Monitoring System Based on IR Absorption", *Optics and Laser Technology*, vol. 40, No. 5, pp. 703-710, Dec. 2007.

*Primary Examiner* — Tarifur R Chowdhury
*Assistant Examiner* — Omar H Nixon
(74) *Attorney, Agent, or Firm* — Blank Rome LLP

(57) ABSTRACT

A multi-channel gas sensor comprising a gas cell (101, 601), a light source (110, 210, 310, 410, 510, 610), a first interference filter (150, 250, 350, 450, 550, 650), a first detection unit (120, 220, 320, 420, 520, 620) and a second detection unit (130, 230, 330, 430, 530, 630). The light source (110, 210, 310, 410, 510, 610) is arranged to emit light radiation into the gas cell (101, 5 601). The first detection unit (120, 220, 320, 420, 520, 620) is arranged to detect light from the light source, that has propagated through at least a part of the gas cell (101, 601), and that has been transmitted through the first interference filter (150, 250, 350, 450, 550, 650). The second detection unit (130, 230, 330, 430, 530, 630) is arranged to be illuminated by light from the light source that has been reflected in the first interference filter (150, 250, 350, 450, 10 550, 650) and then has propagated through the gas cell (101, 601) before illuminating the second detection unit and to detect at least a second wavelength portion of
(Continued)

said light that has been reflected in the first interference filter.

14 Claims, 2 Drawing Sheets

(58) Field of Classification Search
USPC .......................................................... 356/451
See application file for complete search history.

(56) References Cited

U.S. PATENT DOCUMENTS

| | | | | |
|---|---|---|---|---|
| 3,926,556 A | * | 12/1975 | Boucher | A61L 2/12 |
| | | | | 250/435 |
| 3,989,938 A | * | 11/1976 | Auth | G01J 3/453 |
| | | | | 356/451 |
| 6,599,253 B1 | | 7/2003 | Baum et al. | |
| 6,955,652 B1 | | 10/2005 | Baum et al. | |
| 2002/0111043 A1 | * | 8/2002 | Mahawili | H01L 21/67115 |
| | | | | 438/795 |
| 2003/0209669 A1 | * | 11/2003 | Chou | G01N 21/3504 |
| | | | | 250/343 |
| 2004/0104345 A1 | | 6/2004 | Kansakoski et al. | |
| 2004/0203169 A1 | | 10/2004 | Dreyer et al. | |
| 2006/0158648 A1 | | 7/2006 | Matthiessen et al. | |
| 2008/0061238 A1 | | 3/2008 | Hok et al. | |
| 2010/0078563 A1 | | 4/2010 | Haveri et al. | |
| 2018/0188213 A1 | * | 7/2018 | Tumpold | G01N 29/2425 |
| 2018/0202926 A1 | * | 7/2018 | Black | G01N 21/39 |
| 2019/0120754 A1 | | 4/2019 | Schossig et al. | |

FOREIGN PATENT DOCUMENTS

| | | | | |
|---|---|---|---|---|
| DE | 10 2007 043 643 A1 | | 3/2008 | |
| DE | 10 2016 108 544 A1 | | 11/2017 | |
| EP | 0 834 732 A2 | | 4/1998 | |
| EP | 1 332 346 B1 | | 3/2010 | |
| JP | 2018036227 A | * | 3/2018 | |
| WO | WO-2008136958 A1 | * | 11/2008 | A61N 5/06 |
| WO | WO 2014/113287 A1 | | 7/2014 | |

* cited by examiner

MULTI-CHANNEL GAS SENSOR

TECHNICAL FIELD

The present invention relates in general to a gas sensor. In particular, it relates to a multi-channel gas sensor utilizing an interference filter to direct light from a light source, via a gas cell, to a first detection unit and a second detection unit for use in gas detection applications.

BACKGROUND ART

Optical sensing using the absorption bands of various gases in the visible or infrared wavelength range is a method to characterize the content of a gas.

In order to measure the content of a gas by using the absorption bands in a compact unit, the measurement may be performed in a cavity with reflecting surfaces which by several reflections result in an optical path that is longer than the unit. Thereby the length that radiation from a provided radiation source interacts with the gas can be increased and the detection of the gas content can be improved.

To characterize the content of a specific gas it is considered to be advantageous to perform the measurement at a wavelength in which the an absorption band of the specific gas can be measured singularly, thereby minimizing the simultaneous measurement of other gases having similar absorption bands. This will in numerous cases limit the useable wavelengths to measure. In some cases equipment, such as radiation sources and sensors, suitable to measure in the suitable wavelengths are expensive or cumbersome.

It is a known problem that the low concentrations of gas that is provided in sniffing applications require high resolution and high sensitivity in order to detect the limited quantities provided. Similarly, the low concentrations of sample that a separated detection of exhalation gases require higher resolution and higher sensitivity than mouthpiece detection of exhalation gases.

SUMMARY OF THE INVENTION

The aim of the present invention is to set aside the abovementioned drawbacks and shortcomings of the previously known gas sensors and to provide an improved solution for measurements of a gas.

In particular, it is an object to provide a gas sensor for improved detection of low gas concentrations in a compact and inexpensive solution.

The invention is based on the realization that multiple samplings from different channels allows measurements in wavelengths where several gases has coexisting absorption bands. By considering their merged impact on the measurement on the separated channels and from this calculate the gases separated occurrences. Thereby allowing for several simplifications, such as in the radiation source and the detectors used, in a more robust measurement device. For example, should a gas sample be analysed for occurrence of the gases A and B, where the gas A absorbs at the wavelength wA and the gas B absorb at the wavelength wA and wB, it is possible to perform measurements in wB and get a result that can be subtracted from a measurement performed in wA to get a measurement on the gas A without the contribution of gas B. The principle can be expanded to several measurements and overlapping contributions, thereby allowing more precise measurements.

To provide a gas sensor that has an appropriate sensitivity and is reliable in the described conditions is far from trivial. This is especially true if the gas sensor should be able to detect a plurality of substances and not being disturbed by variation in non-measured substances.

Detection of low gas concentrations needed for directed breath, or sniffing applications, require higher resolution than existing affordable solutions. Measurement of several different gases simultaneously are also needed for contactless breath, or sniffing applications, to calculate actual dilution, but the existing multi-gas sensing solutions are expensive, bulky, and consumes a lot of electrical power. Low concentration gas measurements on the other hand are often limited of cross sensitivity of other much more abundant gases present simultaneously.

In view of the above, a general object of the present disclosure is to provide an improved gas sensor that allows improved measurements of a gas by use of a multi-channel measurement.

The object of the invention is met in a multi-channel gas sensor as defined in the appending claims.

In a first aspect, the present invention relates to a multi-channel gas sensor. The multi-channel gas sensor comprise a gas cell, a light source, a first interference filter, a first detection unit and a second detection unit.

The gas cell is arranged to carry the gas. The light source is arranged to emit light radiation into the gas cell. The first interference filter is arranged to be illuminated by light emitted from the light source, which has propagated through at least a part of the gas cell, and configured to transmit a first wavelength portion of the light radiation and to reflect light radiation outside of the first wavelength portion. The first detection unit arranged to detect light from the light source that has been transmitted through the first interference filter. The second detection unit arranged to be illuminated by light from the light source that has been reflected in the first interference filter and to detect at least a second wavelength portion of said light that has been reflected in the first interference filter. The second detection unit is arranged so that the second wavelength portion that is reflected in the first interference filter has propagated in the gas cell before illuminating the second detection unit.

By propagation in the gas cell is meant that the light propagates through at least a part of the gas cell.

Thus, the propagation path in the gas cell is different for the light illuminating the first detection unit and the light illuminating the second detection unit.

By this, a multi-channel gas sensor for measuring at different wavelengths may be provided. For example, different gas specific spectral wavelengths can be tapped out from the gas cell at different propagation paths, separated at well-defined intermediate image points formed on specific points of the gas cell. The point of the gas cell where the selected image is formed an optical interference filter can be arranged. The interference filter transmit the wavelength band associated with the molecular absorption for one or several of the target gases to a detection unit, whereas the out-of-band radiation is reflected and hence this radiation continue propagate unaffected in the gas cell and can be used in a similar way to detect other absorption bands at other wavelengths.

By using an interference filter instead of a dichroic mirror to divide the light into different wavelength portions the need for an additional narrow band filter in front of the detector may be obviated. The interference filter may take both the function of dividing the light into wavelength portions and of narrow band filtering.

Hence, by utilizing measuring at different wavelengths, these measurements may be used in compensation calculation. For example spectral cross-sensitivity for water vapour at 3.4 µm may be eliminated by using the water absorption information gained at 2.7 µm.

In embodiments, the light radiation is mid infrared, IR, radiation and the first interference filter may be configured to reflect mid-IR radiation outside of the first wavelength portion.

Utilizing light radiation in the mid-IR range offers several advantages, such as size and cost, but has been burdened by high spectral cross-sensitivity to many substances. By utilizing multi-pass gas sensor according to the present disclosure, an improved gas sensor may be achieved.

In embodiments, the multi-channel gas sensor may further comprise a second interference filter. The second interference filter may be arranged to be illuminated by light from the light source that has been reflected in the first interference filter. The second interference filter may further be configured to transmit the second wavelength portion of the mid-IR radiation and to reflect mid-IR radiation outside of the second wavelength portion. The second detection unit may be arranged to detect light from the light source that has been transmitted through the second interference filter.

In embodiments, the multi-channel gas sensor may further comprise a third detection unit arranged to be illuminated by light from the light source that has been reflected in the second interference filter and to detect at least a third wavelength portion of said light that has been reflected in the second interference filter.

In embodiments, the first detection unit may be arranged to detect a $CO_2$ peak at 4.26 µm, the second detection unit may be arranged to detect a $H_2O$ peak at 2.66 µm and the third detection unit may be arranged to detect an ethanol peak at 3.41 µm. A detection unit may be arranged to detect a wavelength by adapting the corresponding interference filter to transmit the corresponding wavelength portion to that detection unit, by having a filter arranged in front of the detection unit, and/or having a detection span suitable for that wavelength. By this, the multi-channel gas sensor may be adapted to detect ethanol and be used in for example alcohol lock investigations and screening demonstrations.

In embodiments, the multi-channel gas sensor may comprise a computational unit that is arranged with a correlation algorithm to calculate the diffusion factor needed for estimating the breath alcohol concentration and blood alcohol level.

In embodiments, the first detection unit may be arranged to detect a $CO_2$ peak at 4.26 µm, the second detection unit may be arranged to detect a $H_2O$ peak at 2.66 µm and the third detection unit may be arranged to detect an R32 peak at 3.37 µm. A detection unit may be arranged to detect a wavelength by adapting the corresponding interference filter to transmit the corresponding wavelength portion to that detection unit, by having a filter arranged in front of the detection unit, and/or having a detection span suitable for that wavelength. By this, the multi-channel gas sensor may be adapted to detect R32 and other hydrocarbons and be used in for example Freon detection, leak detections and similar.

In embodiments, the first detection unit may be arranged to detect a $C_xH_y$ peak at 3.45 µm, the second detection unit may be arranged to detect a $H_2O$ peak at 2.66 µm and the third detection unit may be arranged to detect and a methane peak at 3.32 µm. A detection unit may be arranged to detect a wavelength by adapting the corresponding interference filter to transmit the corresponding wavelength portion to that detection unit, by having a filter arranged in front of the detection unit, and/or having a detection span suitable for that wavelength. By this, the multi-channel gas sensor may be adapted to detect methane and be used in for example methane surveillance, leak detection, landfills emission monitoring.

In embodiments, the first detection unit may be arranged to detect a $CO_2$ peak at 4.26 µm, the second detection unit may be arranged to detect a $H_2O$ peak at 2.66 µm and the third detection unit may be arranged to detect and a methane peak at 3.32 µm. A detection unit may be arranged to detect a wavelength by adapting the corresponding interference filter to transmit the corresponding wavelength portion to that detection unit, by having a filter arranged in front of the detection unit, and/or having a detection span suitable for that wavelength. By this, the multi-channel gas sensor may be adapted to be used in as a greenhouse gas environmental monitor and be used in for example city emission monitoring and carbon cycle mapping.

In embodiments, the first detection unit may be arranged to detect a $CO_2$ peak at 4.26 µm, the second detection unit may be arranged to detect a $H_2O$ peak at 2.66 µm and the third detection unit may be arranged to detect and a $N_2O$ peak at 4.505 µm. A detection unit may be arranged to detect a wavelength by adapting the corresponding interference filter to transmit the corresponding wavelength portion to that detection unit, by having a filter arranged in front of the detection unit, and/or having a detection span suitable for that wavelength. By this, the multi-channel gas sensor may be adapted to detect nitrous oxide and be used in for example monitoring for greenhouse gas emission in agriculture and monitor for hospital environments.

In embodiments, the first detection unit may be arranged to detect a $CO_2$ peak at 4.26 µm, the second detection unit may be arranged to detect a $H_2O$ peak at 2.66 µm and the third detection unit may be arranged to detect and a CO peak at 4.695 µm. A detection unit may be arranged to detect a wavelength by adapting the corresponding interference filter to transmit the corresponding wavelength portion to that detection unit, by having a filter arranged in front of the detection unit, and/or having a detection span suitable for that wavelength. By this, the multi-channel gas sensor may be adapted to detect carbon monoxide and be used in for example for alarm and monitoring in indoor spaces, such as garages.

In embodiments, the detection of a wavelength peak may be performed in a detection span surrounding the wavelength peak. The detection span may be centred on the wavelength peak or the detection span may comprise the wavelength peak. The width of the detection span may for example be 0.1%, 0.2%, 0.3%, 0.4%, 0.5%, 0.6%, 0.7%, 0.8%, 0.9%, 1%, 2%, 3%, 4%, 5%, 6%, 7%, 8%, 9% or 10% of the wavelength peak. The width of the detection span may be defined by the full width at half maximum, FWHM.

In embodiments, the detection unit may comprise a photodiode detector. The photodiode detector may be tuned to be more sensitive in a wavelength span of interest than in a wavelength span not of interest.

In embodiments, the second detection unit may be arranged so that the second wavelength portion that is reflected in the first interference filter propagates through the gas cell before illuminating the second detection unit.

By this, a multi-channel gas sensor for measuring at different wavelengths may be provided. For example, different gas specific spectral wavelengths can be tapped out from the gas cell at different propagation paths, separated at well-defined intermediate image points formed on specific points of the gas cell. The point of the gas cell where the selected image is formed an optical interference filter can be arranged. The interference filter transmit the wavelength band associated with the molecular absorption for one or several of the target gases to a detection unit, whereas the out-of-band radiation is reflected and hence this radiation continue propagate unaffected in the gas cell and can be used in a similar way to detect other absorption bands at other wavelengths. By providing selective reflections, the multi-channel gas sensor can provide different absorption paths, having different lengths, for different spectral wavelengths.

In embodiments, the multi-channel gas sensor may further comprise a first reflecting surface arranged to reflect IR radiation previously reflected at the first interference filter towards the second interference filter.

In embodiments, the third detection unit may be arranged so that the third wavelength portion is detected after propagation through the gas cell after reflection at the second interference filter.

In embodiments, the multi-channel gas sensor may further comprise a second reflecting surface arranged to reflect IR radiation previously reflected at the second interference filter towards the third interference filter.

In embodiments, the first reflecting surface and/or the second reflecting surface may be curved, thereby acting as collimating reflectors to collect the radiation emitted and/or reflected sideways from the optical axis.

In embodiments, the multi-channel gas sensor may further comprise a third interference filter arranged to be illuminated by light from the light source that has been reflected in the second interference filter. The third interference filter may further be configured to transmit the third wavelength portion of the light radiation to the third detection unit and to reflect light radiation outside of the third wavelength portion. The third detection unit may further be arranged to detect light from the light source that has been transmitted through the third interference filter.

In embodiments, the interference filters may be band pass filters. By the interference filters being band pass filters the need for an additional narrow band filter in front of the detection units is obviated.

The wavelength portions may be chosen to comprise either one wavelength of 2.7 µm, 3.4 µm or 4.25 µm.

In embodiments, the interference filters may be band pass filters and the first wavelength portion is chosen to comprise 3.4 µm, the second wavelength portion is chosen to comprise 2.7 µm and the third wavelength portion is chosen to comprise 4.25 µm.

In embodiments, the light source may comprise a black body radiator and a filter arranged to transmit mid-IR radiation, wherein the filter is arranged between the black body radiator and the gas cell.

In embodiments, the light source may be a quantum photo diode. The quantum photo diode may for example be based on a combination of aluminium, indium and antimony.

In embodiments, the light source may be a bi-pin lamp. The lamp may be miniaturized or sub miniature.

In embodiments, the black body radiator may be a light bulb.

In embodiments, the mid-IR radiation may be IR radiation having a wavelength below 4 µm. In embodiments, the mid-IR radiation may be IR radiation having a wavelength below 5 µm.

In embodiments, the mid-IR radiation may be IR radiation having a wavelength below 6 µm.

In embodiments, the light source may comprise an optical element arranged to shape radiation emitted from the light source. The optical element may have a composition suitable for the emitted radiation. The optical element may for example be a lens, a mirror and/or a shaped tip of the radiation source. An example of a tip may be a tip of the substance at least partly enclosing a radiation emitting diode, such a tip may be shaped to direct the radiation.

In embodiments, the gas cell may be made of melded plastic.

In embodiments, the gas cell may comprise a plurality of part that is attached using welding.

In embodiments, the gas cell may comprise a plurality of part that is attached using glue.

In embodiments, the multi-channel gas sensor may be a nondispersive infrared sensor, NDIR, and the gas cell may be a multi pass cell. By this, the path length inside the cell may be increased. For example, the gas cell may be configured as a White cell. The White cell may be arranged having three spherical, concave mirrors having the same radius of curvature. By rotating the three mirrors the number of reflections in the cell can be controlled and thereby the path length and absorption path.

In embodiments, the propagation of the mid IR radiation from the light source through the cell to the first detection unit via the first interference filter may form a first absorption path. Further, the propagation of the mid IR radiation from the light source through the cell to the second detection unit via the first interference filter, the first reflecting surface and the second interference filter may form a second absorption path. Further, the propagation of the mid IR radiation from the light source through the cell to the third detection unit via the first interference filter, the first reflecting surface, the second interference filter, the second reflecting surface and the third interference filter may form a third absorption path.

In order to perform measurements at different wavelength bands it has been realized that the measurements may be further improved by allowing different lengths of the absorption paths for the respective measurements. By this, a higher quality of the measured signal can be achieved.

In embodiments, the first absorption path length may be 25 cm, the second absorption path length may be 37 cm and the third absorption path length may be 49 cm. The absorption path length is the path length for the light in the gas cell.

In embodiments, the first optical path length in the gas cell may be 25 cm, the second optical path length in the gas cell may be 37 cm and the optical path length in the gas cell may be 49 cm. The optical path length in the gas length is equivalent to the absorption path length. It is possible that the multi-channel gas sensor also includes optical path lengths outside the gas cell, i.e., that the light travels outside the gas cell before hitting the detection unit. Such optical path lengths outside the gas cell has no effect on the measurements with the multi-channel gas sensor.

In embodiments, the gas cell may comprise additional reflective surfaces to increase the optical path length between the different detection units.

In embodiments, the interference filters may be arranged along a first side of the gas cell, and the reflecting surfaces may be arranged along a second side of the gas cell.

In embodiments, the gas cell may further comprise a gas inlet. The gas inlet can for example be used to fill the gas cell with a gas or a gas composition for measurement. The gas inlet may for example be one or a plurality of holes. The gas inlet may comprise a filter, such as a particle filter. The filter may have a composition to provide a limited flow resistance.

In embodiments, the gas inlet may be a diffusion inlet.

In embodiments, the gas cell may further comprise a fan, a pump or similar flow providing arrangements. The flow providing arrangement may be arranged at an inlet and/or an outlet of the gas cell.

In embodiments, the gas cell may further comprise a gas outlet or exit hole. The gas outlet can for example be used to empty the gas cell from a gas or a gas composition. The exit hole may also be used to regulate the pressure of the gas cell. The gas outlet may for example be one or a plurality of holes. The gas outlet may further comprise valve.

In embodiments, the gas outlet may be a diffusion outlet.

In embodiments, the multi-channel gas sensor may comprise a human machine interface, HMI, such as a button or switch that is arranged to switch the multi-channel gas sensor from a first mode to a second mode and/or from a second mode to a first mode. The first mode may be shut down or turned off. The second mode may be operational or turned on.

In embodiments, the multi-channel gas sensor may comprise a human machine interface, HMI, such as a light emitting diode, LED, arranged to provide status information to a user.

In embodiments, the HMI may comprise at least one multi-coloured LED wherein the at least one multi-coloured LED may indicate a result from the multi-channel gas sensor. For example a multi-coloured LED may indicate a measurement well below a set point limit by a first colour, such as green, close to a set limit by a second colour, such as yellow, and above a set limit by a third colour, such as red. A measurement close to a set limit or an unverified measurement may demand a second measurement, this may for example be indicated by a fourth colour or by a blinking LED.

In embodiments, the multi-channel gas sensor may comprise a human machine interface, HMI, such as a button or switch that is arranged to switch the multi-channel gas sensor from a first mode of operation to a second mode of operation and/or from a second mode of operation to a first mode of operation. The first mode of operation may be a fast screening mode. The second mode of operation may be a precise measurement mode.

In embodiments, the multi-channel gas sensor may comprise a human machine interface, HMI, such as a button or switch that may be arranged to switch the multi-channel gas sensor between several operation modes, such as for example single breath measurement, semi continuous breath by breath measurement, continuous sniffing measurement, variable/dynamic measurement and parallel integration time of breath alcohol concentration estimation measurement.

In embodiments, the multi-channel gas sensor may comprise a temperature regulating arrangement. For example a heating unit and/or a cooling unit. The temperature regulating arrangement may be provided in functional connection with the interior of the gas cell or in functional connection with an entrance point, such as a gas inlet. By utilizing a temperature regulating arrangement a thermally stabilized gas cell may be provided, thereby improving the accuracy, resolution and long term stability of the multi-channel gas sensor.

In embodiments, the temperature regulating arrangement may comprise a pre heater arranged to increase the temperature of the gas before entering the gas cell.

In embodiments, the temperature regulating arrangement may be comprised in a pump, a fan or another flow providing arrangement.

By having a sensitive measurement, which may be assisted by a flow providing arrangement, the multi-channel gas sensor may be used for separated measurements, of for example exhalations, thereby providing a simplified and hygienic solution due to the decreased demand of a mouthpiece.

BRIEF DESCRIPTION OF THE DRAWINGS

The invention is described in the following illustrative and non-limiting detailed description of exemplary embodiments, with reference to the appended drawings, wherein.

All figures are schematic, not necessarily to scale, and generally only show parts that are necessary in order to elucidate the invention, wherein other parts may be omitted or merely suggested. Throughout the figures the same reference signs designate the same, or essentially the same features.

DETAILED DESCRIPTION

The present invention can be used to measure gas which overcome or at least mitigate the problems of the prior art and with an improved functionality in a more efficient construction that provides reliability benefits.

Figure 1:
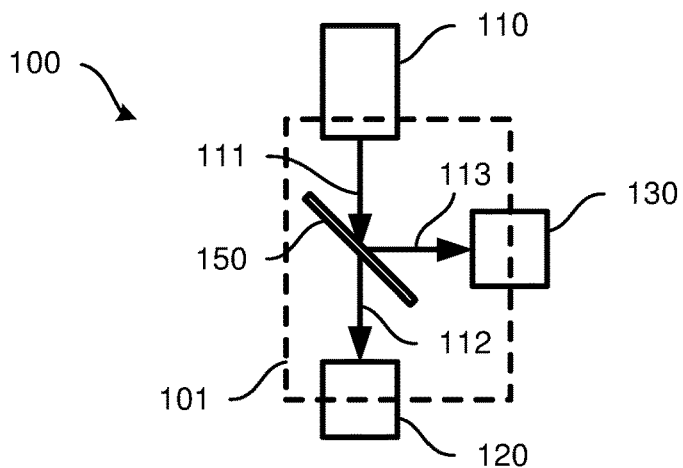
FIG. 1 is a schematic illustration of a multi-channel gas sensor according to an aspect of the present invention.

The invention is described in the following illustrative and non-limiting detailed description of exemplary embodiments, with reference to the appended drawings, wherein:

FIG. 1 shows a schematic illustration of a multi-channel gas sensor 100 having a light source 110, a first interference filter 150, a first detection unit 120 and a second detection unit 130. The light source 110, the first interference filter 150, the first detection unit 120 and the second detection unit 130 are illustrated as at least partially included in a gas cell 101. The inclusion in the gas cell may be physically or functionally. By functionally means that the objects may be arranged outside of the gas cell 101, but in functional communication, for example there may be a window in the gas cell 101 that transmits radiation to a detection unit, that detection unit may then be considered to be functionally included in the gas cell 101. The gas cell 101 is arranged to carry a gas. The light source 110 is arranged to emit light radiation 111 into the gas cell. The first interference filter 150 is arranged to be illuminated by light 111 emitted from the light source 110, which has propagated through at least a part of the gas cell 101, and configured to transmit light radiation 112 having a first wavelength portion of the light radiation and to reflect light radiation 113 outside of the first wavelength portion. The first detection unit 120 arranged to detect light from the light source 110 that has been transmitted through the first interference filter 150. The second detection unit 130 arranged to be illuminated by light 113 from the light source that has been reflected in the first interference filter and to detect at least a second wavelength portion of said light 113 that has been reflected in the first interference filter 150.

The reflecting surfaces, interference filters and beam directions disclosed in the schematic illustration are not necessarily rotated in the correct direction, the objects illustrated are for explanatory purposes and the shown angle of reflection may differ from the angle of reflection resulting from objects oriented in such ways.

Utilizing measuring at different wavelengths, these measurements may be used in compensation calculation. For example spectral cross-sensitivity for water vapour at 3.4 μm may be eliminated by using the water absorption information gained at 2.7 μm.

The light radiation emitted from the light source 110 may be mid infrared, IR, radiation. The light radiation may also be referred to as light, or radiation. Hence the mid-IR radiation may be referred to as mid-IR light or mid-IR light radiation. The first interference filter 150 may configured to reflect mid-IR radiation outside of the first wavelength portion.

The light source 110 may comprise a black body radiator and a filter arranged to transmit mid-IR radiation, wherein the filter is arranged between the black body radiator and the inside of the gas cell. The black body radiator may for example be a light bulb or a diode. The mid-IR radiation may be IR radiation having a wavelength below 5 μm.

The light source 110 may comprise an optical element arranged to shape radiation emitted from the light source 110. The optical element may have a composition suitable for the emitted radiation. The optical element may for example be a lens, a mirror and/or a shaped tip of the radiation source. An example of a tip may be a tip of the substance at least partly enclosing a radiation emitting diode, such a tip may be shaped to direct the radiation.

The detection units may be arranged to detect a specific wavelength span by adapting the corresponding interference filter to transmit the corresponding wavelength portion to that detection unit, by having an additional filter arranged in front of the detection unit, and/or having a detection span of a sensor suitable for that wavelength.

The detection of a wavelength peak may be performed in a detection span surrounding the wavelength peak. The detection span may be centred on the wavelength peak or the detection span may comprise the wavelength peak.

The second detection unit 130 may be arranged so that the second wavelength portion that is reflected in the first interference filter 150 propagates through the gas cell 101 before illuminating the second detection unit 130.

The gas cell 101 may be made of melded plastic, may comprise a plurality of part that is attached using welding or glue.

The gas cell 101 may further comprise a gas inlet. The gas inlet can for example be used to fill the gas cell with a gas or a gas composition for measurement. The gas inlet may for example be one or a plurality of holes. The gas inlet may comprise a filter, such as a particle filter. The filter may have a composition to provide a limited flow resistance. The gas inlet may also be a diffusion inlet.

The gas cell 101 may further comprise a fan, a pump or similar flow providing arrangements. The flow providing arrangement may be arranged at an inlet and/or an outlet of the gas cell.

The gas cell 101 may further comprise a gas outlet or exit hole. The gas outlet can for example be used to empty the gas cell from a gas or a gas composition. The exit hole may also be used to regulate the pressure of the gas cell. The gas outlet may for example be one or a plurality of holes. The gas outlet may further comprise valve. The gas outlet may also be a diffusion outlet.

The multi-channel gas sensor 100 may also comprise a temperature regulating arrangement. For example a heating unit and/or a cooling unit. The temperature regulating arrangement may be provided in functional connection with the interior of the gas cell 101 or in functional connection with an entrance point, such as a gas inlet. By utilizing a temperature regulating arrangement a thermally stabilized gas cell 101 may be provided, thereby improving the accuracy, resolution and long term stability of the multi-channel gas sensor 100. The temperature regulating arrangement may comprise a pre heater arranged to increase the temperature of the gas before entering the gas cell. The temperature regulating arrangement may be comprised in a pump, a fan or another flow providing arrangement.

Figure 2:
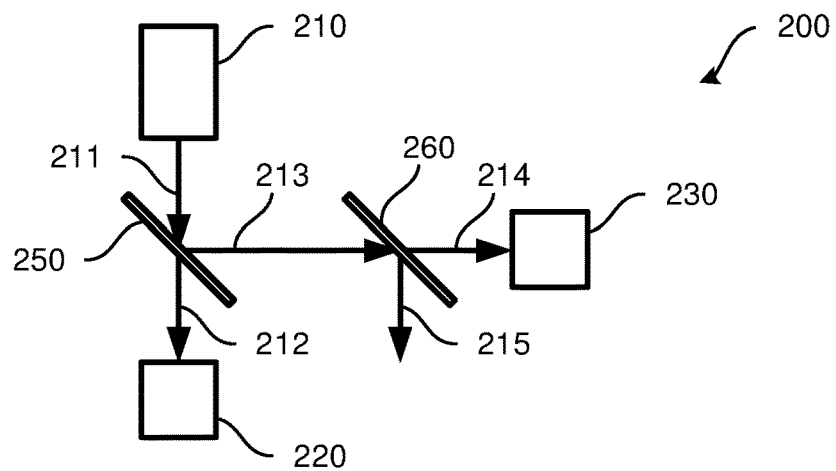
FIG. 2 is a schematic illustration of a multi-channel gas sensor according to an embodiment of the present invention.

FIG. 2 shows a schematic illustration of a multi-channel gas sensor 200 having a light source 210, a first interference filter 250, a second interference filter 260, a first detection unit 220 and a second detection unit 230. The light source 210, the first interference filter 250, the first detection unit 220 and the second detection unit 230 at least partially included in a gas cell. The gas cell is arranged to carry a gas. The light source 210 is arranged to emit light radiation 211 into the gas cell. The first interference filter 250 is arranged to be illuminated by light 211 emitted from the light source 210, which has propagated through at least a part of the gas cell, and configured to transmit light radiation 212 having a first wavelength portion of the light radiation and to reflect light radiation 213 outside of the first wavelength portion. The first detection unit 220 arranged to detect light from the light source 210 that has been transmitted through the first interference filter 250. The second detection unit 230 arranged to be illuminated by light 213 from the light source that has been reflected in the first interference filter and to detect at least a second wavelength portion of said light 213 that has been reflected in the first interference filter 250. The second interference filter 260 is arranged to be illuminated by light 213 from the light source 210 that has been reflected in the first interference filter 250 and after reflection in the first interference filter 250 has propagated through the gas cell 101. The second interference filter 260 is further configured to transmit light radiation 214 of the second wavelength portion of the mid-IR radiation and to reflect mid-IR radiation 215 outside of the second wavelength portion. The second detection unit 230 is arranged to detect light 214 from the light source that has been transmitted through the second interference filter 260.

The multi-channel gas sensor 200 may have an absorbing portion or an exit arranged to allow the radiation that is not detected to be absorbed or exit the gas cell.

Figure 3:
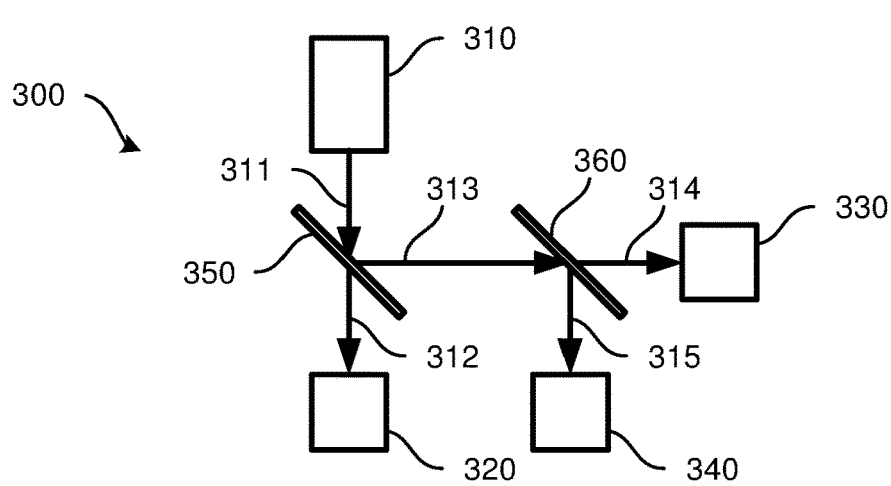
FIG. 3 is a schematic illustration of a multi-channel gas sensor according to an embodiment of the present invention.

FIG. 3 shows a schematic illustration of a multi-channel gas sensor 300 having a light source 310, a first interference filter 350, a second interference filter 360, a first detection unit 320, a second detection unit 330 and a third detection unit 340. The light source 310, the first interference filter 350, the first detection unit 320 and the second detection unit 330 at least partially included in a gas cell. The gas cell is arranged to carry a gas. The light source 310 is arranged to emit light radiation 311 into the gas cell. The first interference filter 350 is arranged to be illuminated by light 311 emitted from the light source 310, which has propagated through at least a part of the gas cell, and configured to transmit light radiation 312 having a first wavelength portion of the light radiation and to reflect light radiation 313 outside of the first wavelength portion. The first detection unit 320 arranged to detect light from the light source 310 that has been transmitted through the first interference filter 350. The second detection unit 330 is arranged to be illuminated by light 313 from the light source that has been reflected in the first interference filter 350, and after reflection in the first interference filter 350 has propagated in the gas cell 101, and to detect at least a second wavelength portion of said light 313 that has been reflected in the first interference filter 350. The second interference filter 360 is arranged to be illuminated by light 313 from the light source 310 that has been reflected in the first interference filter 350, and after reflection in the first interference filter 350 has propagated in the gas cell 101. The second interference filter 360 is further configured to transmit light radiation 314 of the second wavelength portion of the mid-IR radiation and to reflect mid-IR radiation 315 outside of the second wavelength portion. The second detection unit 330 is arranged to detect light 314 from the light source that has been transmitted through the second interference filter 360. The third detection unit 340 is arranged to be illuminated by light 315 from the light source 310 that has been reflected in the second interference filter 360, and after reflection in the second interference filter 360 preferably has propagated in the gas cell 101, and to detect at least a third wavelength portion of said light 315 that has been reflected in the second interference filter 360. Thus, the light that illuminates the second detection unit has a longer propagation path in the gas cell than the light that illuminates the first detection. Correspondingly, the light that illuminates the third detection unit preferably has a longer propagation path in the gas cell than the light that illuminates the second detection.

The interference filters may be band pass filters and the wavelength portion may be chosen to comprise either one wavelength of 2.7 µm, 3.4 µm or 4.25 µm. The interference filters may also be band pass filters and the first wavelength portion may be chosen to comprise 3.4 µm, the second wavelength portion may be chosen to comprise 2.7 µm and the third wavelength portion may be chosen to comprise 4.25 µm.

For example, the first detection unit 320 may be arranged to detect a $CO_2$ peak at 4.26 µm, the second detection unit 330 may be arranged to detect a $H_2O$ peak at 2.66 µm and the third detection unit 340 may be arranged to detect an ethanol peak at 3.41 µm.

For example, the first detection unit 320 may be arranged to detect a $CO_2$ peak at 4.26 µm, the second detection unit 330 may be arranged to detect a $H_2O$ peak at 2.66 µm and the third detection unit 340 may be arranged to detect an R32 peak at 3.37 µm.

For example, the first detection unit 320 may be arranged to detect a $C_xH_y$ peak at 3.45 µm, the second detection unit 330 may be arranged to detect a $H_2O$ peak at 2.66 µm and the third detection unit 340 may be arranged to detect and a methane peak at 3.32 µm.

For example, the first detection unit 320 may be arranged to detect a $CO_2$ peak at 4.26 µm, the second detection unit 330 may be arranged to detect a $H_2O$ peak at 2.66 µm and the third detection unit 340 may be arranged to detect and a methane peak at 3.32 µm.

For example, the first detection unit 320 may be arranged to detect a $CO_2$ peak at 4.26 µm, the second detection unit 330 may be arranged to detect a $H_2O$ peak at 2.66 µm and the third detection unit 340 may be arranged to detect and a $N_2O$ peak at 4.505 µm.

For example, the first detection unit 320 may be arranged to detect a $CO_2$ peak at 4.26 µm, the second detection unit 330 may be arranged to detect a $H_2O$ peak at 2.66 µm and the third detection unit 340 may be arranged to detect and a CO peak at 4.695 µm.

The detection units may comprise a photodiode detector. The photodiode detector may be tuned to be more sensitive in a wavelength span of interest than in a wavelength span not of interest.

The detection units may also be arranged to detect a specific wavelength span by adapting the corresponding interference filter to transmit the corresponding wavelength portion to that detection unit, by having an additional filter arranged in front of the detection unit, and/or having a detection span of a sensor suitable for that wavelength.

The detection of a wavelength peak may be performed in a detection span surrounding the wavelength peak. The detection span may be centred on the wavelength peak or the detection span may comprise the wavelength peak.

The third detection unit 340 is arranged so that the third wavelength portion is detected after propagation through the gas cell after reflection at the second interference filter 360.

The multi-channel gas sensor 300 may have an absorbing portion or an exit arranged to allow the radiation that is not detected to be absorbed or to exit the gas cell.

Figure 4:
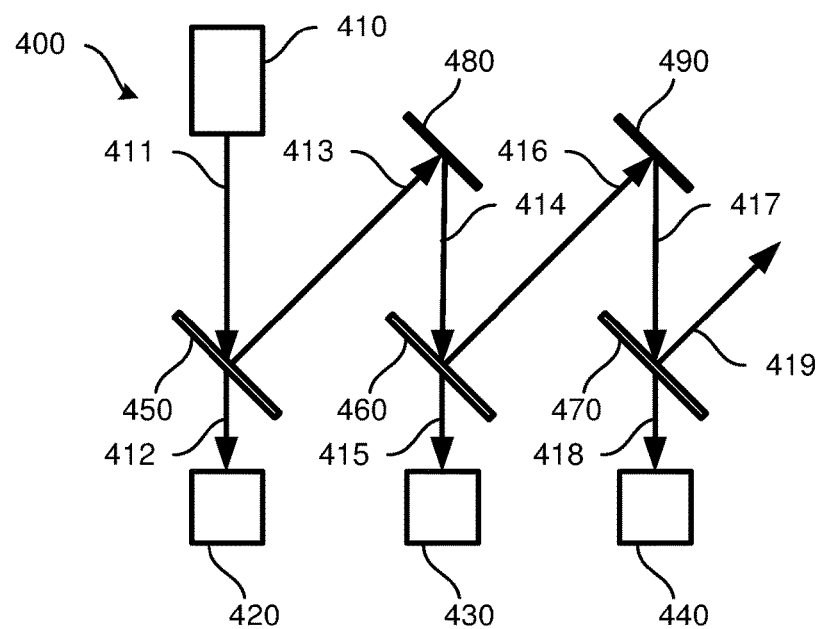
FIG. 4 is a schematic illustration of a multi-channel gas sensor according to an embodiment of the present invention.

FIG. 4 shows a schematic illustration of a multi-channel gas sensor 400 having a light source 410, a first interference filter 450, a second interference filter 460, a first detection unit 420, a second detection unit 430, a third detection unit 440, a first reflecting surface 480 and second reflecting surface 490. The light source 410, the first interference filter 450, the first detection unit 420 and the second detection unit 430 at least partially included in a gas cell. The gas cell is arranged to carry a gas. The light source 410 is arranged to emit light radiation 411 into the gas cell. The first interference filter 450 is arranged to be illuminated by light 411 emitted from the light source 410, which has propagated through at least a part of the gas cell, and configured to transmit light radiation 412 having a first wavelength portion of the light radiation and to reflect light radiation 413 outside of the first wavelength portion. The first detection unit 420 arranged to detect light from the light source 410 that has been transmitted through the first interference filter 450. The second detection unit 430 arranged to be illuminated by light 414 from the light source that has been reflected in the first interference filter and the first reflective surface 480, and after reflection in the first interference filter 450 has propagated in the gas cell 101, and to detect at least a second wavelength portion of said light that has been reflected in the first interference filter 450 and the first reflective surface 480, and after reflection in the first interference filter 450 has propagated in the gas cell 101. The second interference filter 460 is arranged to be illuminated by light 414 from the light source 410 that has been reflected in the first interference filter 450 and the first reflective surface 480. The second interference filter 460 is further configured to transmit light radiation 415 of the second wavelength portion of the mid-IR radiation and to reflect mid-IR radiation 416 outside of the second wavelength portion. The second detection unit 430 is arranged to detect light 415 from the light source that has been transmitted through the second interference filter 460. The third detection unit 440 is arranged to be illuminated by light 415 from the light source 410 that has been reflected in the second interference filter 460 and the second reflective surface 490, and after reflection in the second interference filter 460 preferably has propagated in the gas cell 101, and to detect at least a third wavelength portion of said light 418 that has been reflected in the second interference filter 460 and the second reflective surface 490, and after reflection in the second interference filter 460 preferably has propagated in the gas cell 101.

The propagation of the mid IR radiation from the light source 410 through the gas cell to the first detection unit 420 via the first interference filter 450 may form a first absorption path. Further, the propagation of the mid IR radiation from the light source 410 through the cell to the second detection unit 430 via the first interference filter 450, the first reflecting surface 480 and the second interference filter 460 may form a second absorption path. Further, the propagation of the mid IR radiation from the light source 410 through the cell to the third detection unit 440 via the first interference filter 450, the first reflecting surface 480, the second interference filter 460, the second reflecting surface 490 and the third interference filter 470 may form a third absorption path.

The first reflecting surface 480 and the second reflecting surface 490 may be curved, thereby acting as collimating reflectors to collect the radiation emitted and/or reflected sideways from the optical axis The interference filters may be arranged along a first side of the gas cell, and the reflecting surfaces may be arranged along a second side of the gas cell.

Figure 5:
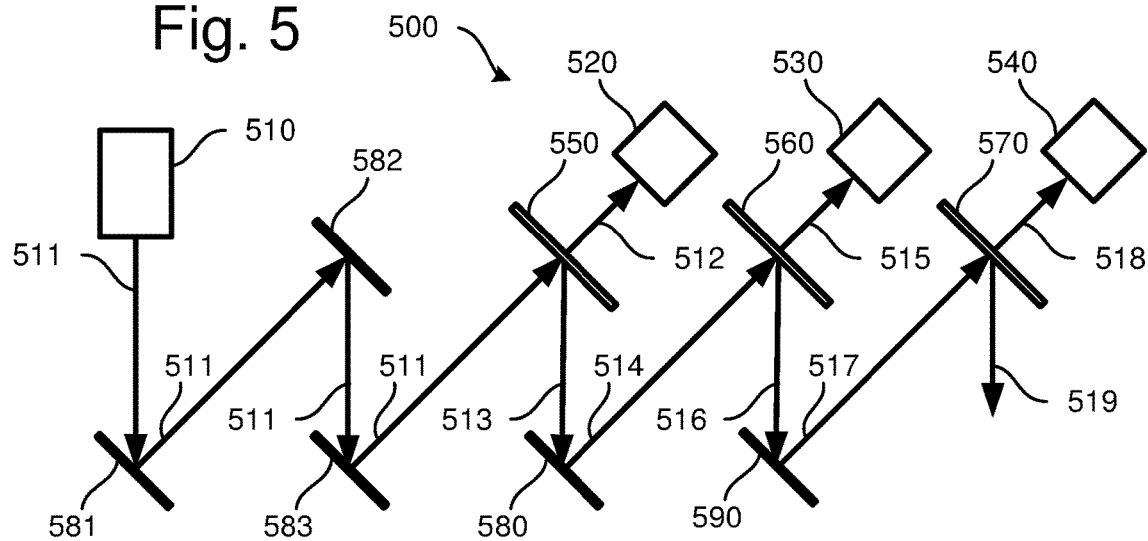
FIG. 5 is a schematic illustration of a multi-channel gas sensor according to an embodiment of the present invention.

FIG. 5 shows a schematic illustration of a multi-channel gas sensor 500 having a light source 510, a first interference filter 550, a second interference filter 560, a first detection unit 520, a second detection unit 530, a third detection unit 540, a first reflecting surface 580, a second reflecting surface 590 and additional reflective surfaces 581, 582, 583. The light source 510, the first interference filter 550, the first detection unit 520 and the second detection unit 530 at least partially included in a gas cell. The gas cell is arranged to carry a gas. The light source 510 is arranged to emit light radiation 511 into the gas cell. The light radiation 511 emitted from the light source 510 is reflected on the additional reflective surfaces 581, 582, 583 to increase the optical path length for the light inside the gas cell, thereby increasing the absorption path length. The first interference filter 550 is arranged to be illuminated by light 511 emitted from the light source 510, which has propagated through the gas cell via the additional reflective surfaces 581, 582, 583, and configured to transmit light radiation 512 having a first wavelength portion of the light radiation and to reflect light radiation 513 outside of the first wavelength portion. The first detection unit 520 arranged to detect light from the light source 510 that has been transmitted through the first interference filter 550. The second detection unit 530 arranged to be illuminated by light 514 from the light source that has been reflected in the first interference filter and the first reflective surface 580 and to detect at least a second wavelength portion of said light that has been reflected in the first interference filter 550 and the first reflective surface 580. The second interference filter 560 is arranged to be illuminated by light 514 from the light source 510 that has been reflected in the first interference filter 550 and the first reflective surface 580. The second interference filter 560 is further configured to transmit light radiation 515 of the second wavelength portion of the mid-IR radiation and to reflect mid-IR radiation 516 outside of the second wavelength portion. The second detection unit 530 is arranged to detect light 515 from the light source that has been transmitted through the second interference filter 560. The third detection unit 540 is arranged to be illuminated by light 515 from the light source 510 that has been reflected in the second interference filter 560 and the second reflective surface 590 and to detect at least a third wavelength portion of said light 518 that has been reflected in the second interference filter 560 and the second reflective surface 590. Between each reflection in an interference filter the light preferably propagates in the gas cell.

Additional reflective surfaces may also be provided between the first interference filter 550 and the second interference filter 560 and/or the second interference filter 560 and the third interference filter 570 in order to further increase the optical path length between the different detection units. The additional reflective surfaces may be curved, thereby acting as collimating reflectors to collect the radiation emitted and/or reflected sideways from the optical axis.

Figure 6A:
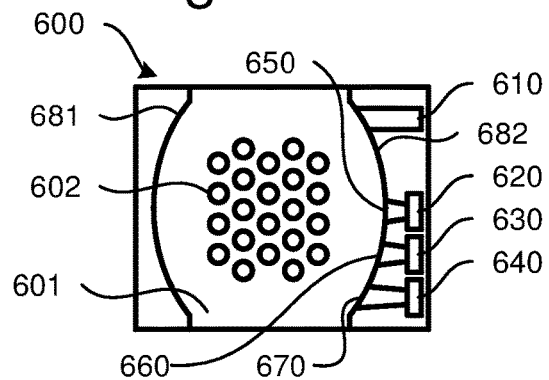
FIG. 6a is a schematic illustration of a multi-channel gas sensor according to an embodiment of the present invention.

FIG. 6a shows a schematic illustration of a multi-channel gas sensor 600 having a gas inlet 602, a light source 610, a first interference filter 650, a second interference filter 660, a third interference filter 670, a first detection unit 620, a second detection unit 630, a third detection unit 640 and a reflecting surface 681. The light source 610, the first interference filter 650, the first detection unit 620 and the second detection unit 630 at least partially included in a gas cell. The gas cell is arranged to carry a gas. The light source 610 is arranged to emit light radiation into the gas cell. The light radiation emitted from the light source 610 is reflected on the reflective surface 681 to increase the optical path length for the light inside the gas cell, thereby increasing the absorption path length. The first interference filter 650 is arranged to be illuminated by light emitted from the light source 610, which has propagated through the gas cell via the reflective surface 681, and configured to transmit light radiation having a first wavelength portion of the light radiation and to reflect light radiation outside of the first wavelength portion. The first detection unit 620 arranged to detect light from the light source 610 that has been transmitted through the first interference filter 650. The second detection unit 630 arranged to be illuminated by light from the light source that has been reflected in the first interference filter and the reflective surface 681 and to detect at least a second wavelength portion of said light that has been reflected in the first interference filter 650 and the reflective surface 681. The second interference filter 660 is arranged to be illuminated by light from the light source 610 that has been reflected in the first interference filter 650 and the reflective surface 681. The second interference filter 660 is further configured to transmit light radiation of the second wavelength portion of the mid-IR radiation and to reflect mid-IR radiation outside of the second wavelength portion. The second detection unit 630 is arranged to detect light from the light source that has been transmitted through the second interference filter 660. The third detection unit 640 is arranged to be illuminated by light from the light source 610 that has been reflected in the second interference filter 660 and the reflective surface 681 and to detect at least a third wavelength portion of said light that has been reflected in the second interference filter 660 and the reflective surface 681.

The gas inlet 602 can for example be used to fill the gas cell with a gas or a gas composition for measurement. The gas inlet 602 may for example be one or a plurality of holes. The gas inlet 602 may comprise a filter, such as a particle filter. The filter may have a composition to provide a limited flow resistance. The gas inlet 602 may also be a diffusion inlet. The gas inlet 602 may comprise a fan, a pump or similar flow providing arrangements.

The gas cell may further comprise a gas outlet or exit hole. The gas outlet can for example be used to empty the gas cell from a gas or a gas composition. The exit hole may also be used to regulate the pressure of the gas cell. The gas outlet may for example be one or a plurality of holes. The gas outlet may further comprise valve. The gas outlet may also be a diffusion outlet. The gas outlet may be arranged on another side than the gas inlet 602.

The first interference filter 650, the second interference filter 660 and the third interference filter 670 may form a continuous reflective surface 682.

Figure 6B:
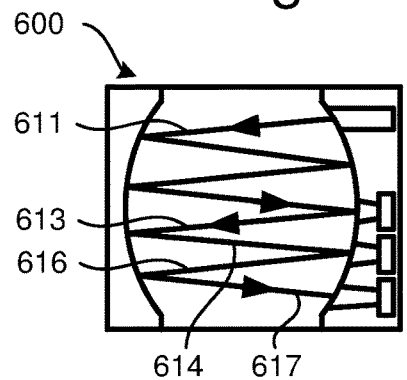
FIG. 6b is a schematic illustration of a beam path in a multi-channel gas sensor according to an embodiment of the present invention.

FIG. 6*b* shows a schematic illustration of a beam path in a multi-channel gas sensor 600 having a light source, a first interference filter, a second interference filter, a third interference filter, a first detection unit, a second detection unit, a third detection unit and a reflecting surface. The light source, the first interference filter, the first detection unit and the second detection unit at least partially included in a gas cell. The gas cell is arranged to carry a gas. The light source is arranged to emit light radiation 611 into the gas cell. The light radiation 611 emitted from the light source is reflected on the reflective surface to increase the optical path length for the light inside the gas cell, thereby increasing the absorption path length. The first interference filter is arranged to be illuminated by light 611 emitted from the light source, which has propagated through the gas cell via the reflective surface, and configured to transmit light radiation having a first wavelength portion of the light radiation and to reflect light radiation 613 outside of the first wavelength portion. The first detection unit arranged to detect light from the light source that has been transmitted through the first interference filter. The second detection unit arranged to be illuminated by light 614 from the light source that has been reflected in the first interference filter and the reflective surface and to detect at least a second wavelength portion of said light that has been reflected in the first interference filter and the reflective surface. The second interference filter is arranged to be illuminated by light 614 from the light source that has been reflected in the first interference filter and the reflective surface. The second interference filter is further configured to transmit light radiation of the second wavelength portion of the mid-IR radiation and to reflect mid-IR radiation 616 outside of the second wavelength portion. The second detection unit is arranged to detect light from the light source that has been transmitted through the second interference filter. The third detection unit is arranged to be illuminated by light 617 from the light source that has been reflected in the second interference filter and the reflective surface and to detect at least a third wavelength portion of said light that has been reflected in the second interference filter and the reflective surface.

The cell may be a multi-pass cell, this is for example shown in the 6*b* figure. By arranging the cell to be a multi-pass cell, the path length inside the cell may be increased. For example, the gas cell may be configured as a White cell. The White cell may be arranged having three spherical, concave mirrors having the same radius of curvature. In the case shown in FIG. 6*b*, the reflecting surface 681 may be comprised of several mirror elements, such as for example two spherical, concave mirrors having the same radius of curvature. The first interference filter, the second interference filter and the third interference filter may form a continuous reflective surface that may be a spherical, concave mirror having the same radius of curvature as the two spherical, concave mirrors. By rotating the three mirrors the number of reflections in the cell can be controlled and thereby the path length and absorption path.

The beam path shown in the figures, such as 6*b*, are for schematic illustration of the beam path a in a multi-channel gas sensor. The directions of the beam between the different elements may differ from the illustration.

The multi-channel gas sensor may also comprise a human machine interface, HMI, such as a button or switch that may be arranged to switch the multi-channel gas sensor from a first mode to a second mode and/or from a second mode to a first mode. The first mode may be shut down or turned off. The second mode may be operational or turned on.

The multi-channel gas sensor may also comprise a human machine interface, HMI, such as a light emitting diode, LED, arranged to provide status information to a user. The LED arrangement may be at least one multi-coloured LED wherein the at least one multi-coloured LED may indicate a result from the multi-channel gas sensor. For example a multi-coloured LED may indicate a measurement well below a set point limit by a first colour, such as green, close to a set limit by a second colour, such as yellow, and above a set limit by a third colour, such as red. A measurement close to a set limit or an unverified measurement may demand a second measurement, this may for example be indicated by a fourth colour or by a blinking LED.

The multi-channel gas sensor may also comprise a human machine interface, HMI, such as a button or switch that is arranged to switch the multi-channel gas sensor from a first mode of operation to a second mode of operation and/or from a second mode of operation to a first mode of operation. The first mode of operation may be a fast screening mode. The second mode of operation may be a precise measurement mode.

The multi-channel gas sensor may also comprise a human machine interface, HMI, such as a button or switch that is arranged to switch the multi-channel gas sensor between several operation modes, such as for example single breath measurement, semi continuous breath by breath measurement, continuous sniffing measurement, variable/dynamic measurement and parallel integration time of breath alcohol concentration estimation measurement.

In block diagrams, illustrated components are depicted as discrete functional blocks, but embodiments are not limited to systems in which the functionality described herein is organized as illustrated. The functionality provided by each of the components may be provided by hardware modules that are differently organized than is presently depicted. The control of the system described herein may be provided by one or more processors of one or more computers executing code stored on a tangible, non-transitory, machine readable medium. In some cases, notwithstanding use of the singular term "medium", the instructions may be distributed on different storage devices associated with different computing devices, for instance, with each computing device having a different subset of the instructions. Such implementation shall be considered consistent with usage of the singular term "medium" herein. In some cases, third party content delivery networks may host some or all of the information conveyed over networks, in which case, to the extent the information (e.g. content) is said to be supplied or otherwise provided, the information may be provided by sending instructions to retrieve that information from a content delivery network.

While specific embodiments have been described, the skilled person will understand that various modifications and alterations are conceivable within the scope as defined in the appended claims.

The invention claimed is:

1. A multi-channel gas sensor, comprising
a multi-pass gas cell arranged to carry the gas;
a light source arranged to emit light radiation into the gas cell;
a first interference filter arranged to be illuminated by light emitted from the light source, which has propagated through at least a part of the gas cell, and configured to transmit a first wavelength portion of the light radiation and to reflect light radiation outside of the first wavelength portion;
a first detection unit arranged to detect light from the light source that has been transmitted through the first interference filter; and
a second detection unit arranged to be illuminated by light from the light source that has been reflected in the first interference filter and to detect at least a second wavelength portion of said light that has been reflected in the first interference filter,
a reflecting surface comprising two concave mirrors,
wherein the first interference filter is arranged along a mirror,
wherein the mirror, the first interference filter, the first detection unit and the second detection unit are arranged along a first side of the multi-pass gas cell, and the reflecting surface comprising two concave mirrors is arranged along a second side of the multi-pass gas cell, and
wherein the second detection unit is arranged so that the second wavelength portion that is reflected in the first interference filter has propagated in the gas cell before illuminating the second detection unit.

2. A multi-channel gas sensor according to claim 1, wherein the light radiation is mid infrared, IR, radiation, and the first interference filter is configured to reflect mid-IR radiation outside of the first wavelength portion.

3. A multi-channel gas sensor according to claim 2, further comprising:
a second interference filter arranged to be illuminated by light from the light source that has been reflected in the first interference filter and configured to transmit the second wavelength portion of the mid-IR radiation and to reflect mid-IR radiation outside of the second wavelength portion, wherein the second detection unit is arranged to detect light from the light source that has been transmitted through the second interference filter, wherein the second interference filter is arranged along the same mirror as the first interference filter.

4. A multi-channel gas sensor according to claim 3, further comprising:
a third detection unit arranged to be illuminated by light from the light source that has been reflected in the second interference filter and to detect at least a third wavelength portion of said light that has been reflected in the second interference filter.

5. A multi-channel gas sensor according to claim 4, wherein the third detection unit is arranged so that the third wavelength portion is detected after propagation through the gas cell after reflection at the second interference filter.

6. A multi-channel gas sensor according to claim 3, further comprising:
a third interference filter arranged to be illuminated by light from the light source that has been reflected in the second interference filter and configured to transmit the third wavelength portion of the light radiation to the third detection unit and to reflect light radiation outside of the third wavelength portion, wherein the third detection unit is arranged to detect light from the light source that has been transmitted through the third interference filter, and wherein the third interference filter is arranged along the same mirror as the first interference filter.

7. A multi-channel gas sensor according to claim 3, wherein the interference filters are band pass filters.

8. A multi-channel gas sensor according to claim 7, wherein the wavelength portions are chosen to comprise either one wavelength of 2.7 μm, 3.4 μm or 4.25 μm.

9. A multi-channel gas sensor according to claim 3, wherein the interference filters are band pass filters;
the first wavelength portion is chosen to comprise 3.4 μm;
the second wavelength portion is chosen to comprise 2.7 μm; and
the third wavelength portion is chosen to comprise 4.25 μm.

10. A multi-channel gas sensor according to claim 1, wherein the light source comprises a black body radiator and a filter arranged to transmit mid-IR radiation, and wherein the filter is arranged between the black body radiator and the gas cell.

11. A multi-channel gas sensor according to claim 10, wherein the black body radiator is a light bulb.

12. A multi-channel gas sensor according to claim 10, wherein mid-IR radiation is IR radiation having a wavelength below 5 μm.

13. A multi-channel gas sensor according to claim 1, wherein the gas cell is made of molded plastic.

14. A multi-channel gas sensor according to claim 1, wherein the multi-channel gas sensor is a nondispersive infrared sensor, NDIR.

* * * * *